(12) United States Patent
McBroom et al.

(10) Patent No.: US 7,485,782 B1
(45) Date of Patent: Feb. 3, 2009

(54) SOYBEAN CULTIVAR S06-02JR409114

(75) Inventors: Roger L. McBroom, St Joseph, IL (US); Julia L. Brown, Sidell, IL (US)

(73) Assignee: Syngenta Participation AG, Basel (CH)

( * ) Notice: Subject to any disclaimer, the term of this patent is extended or adjusted under 35 U.S.C. 154(b) by 0 days.

(21) Appl. No.: 11/879,852

(22) Filed: Jul. 19, 2007

Related U.S. Application Data

(60) Provisional application No. 60/833,952, filed on Jul. 28, 2006.

(51) Int. Cl.
*A01H 1/00* (2006.01)
*A01H 4/00* (2006.01)
*A01H 5/00* (2006.01)
*A01H 5/10* (2006.01)
*C12N 15/82* (2006.01)

(52) U.S. Cl. .................. 800/312; 800/260; 800/278; 800/279; 800/281; 800/284; 800/298; 800/300; 800/301; 800/302; 800/303; 435/415; 435/426

(58) Field of Classification Search .................. None
See application file for complete search history.

*Primary Examiner*—Russell Kallis
(74) *Attorney, Agent, or Firm*—Dana S. Rewoldt

(57) ABSTRACT

The present invention is in the field of soybean variety S06-02JR409114 breeding and development. The present invention particularly relates to the soybean variety S06-02JR409114 and its progeny, and methods of making S06-02JR409114.

15 Claims, 2 Drawing Sheets

US 7,485,782 B1

SOYBEAN CULTIVAR S06-02JR409114

REFERENCE TO RELATED APPLICATION

This application claims the benefit under Title 35, United States Code, § 119(e) of U.S. provisional application 60/833,952 filed Jul. 28, 2006.

THE FIELD OF THE INVENTION

The present invention is in the field of soybean variety breeding and development. The present invention particularly relates to the soybean variety S06-02JR409114 and its progeny, and methods of making.

BACKGROUND OF THE INVENTION

Soybean Glycine max (L) is an important oil seed crop and a valuable field crop. However, it began as a wild plant. This plant and a number of other plants have been developed into valuable agricultural crops through years of breeding and development. The pace of the development of soybeans, into an animal foodstuff and as an oil seed has dramatically increased in the last one hundred years. Planned programs of soybean breeding have increased the growth, yield and environmental hardiness of the soybean germplasm.

Due to the sexual reproduction traits of the soybean, the plant is basically self-pollinating. A self-pollinating plant permits pollen from one flower to be transferred to the same or another flower of the same plant. Cross-pollination occurs when the flower is pollinated with pollen from a different plant; however, soybean cross-pollination is a rare occurrence in nature.

Thus the growth and development of new soybean germplasm requires intervention by the breeder into the pollination of the soybean. The breeders' methods of intervening in the pollination depend on the type of trait that is being bred. Soybeans are developed for a number of different types of traits morphological (form and structure), phenotypical, or for traits like growth, day length, temperature requirements, initiation date of floral or reproductive development, fatty acid content, insect resistance, disease resistance, nematode resistance, fungal resistance, herbicide resistance, tolerance to various environmental factors like drought, heat, wet, cold, wind, adverse soil condition and also for yield. The genetic complexity of the trait often drives the selection of the breeding method.

Due to the number of genes within each chromosome, millions of genetic combinations exist in the breeders' experimental soybean material. This genetic diversity is so vast that a breeder cannot produce the same two cultivars twice using the exact same starting parental material. Thus, developing a single variety of useful commercial soybean germplasm is highly unpredictable, and requires intensive research and development.

The development of new soybeans comes through breeding techniques, such as: recurrent selection, mass selections, backcrossing, single seed descent and multiple seed procedure. Additionally, marker assisted breeding allows more accurate movement of desired alleles or even specific genes or sections of chromosomes to be moved within the germplasm that the breeder is developing. RFLP, RAPD, AFLP, SSR, SNP, SCAR, isozymes, are some of the forms of markers that can be employed in breeding soybeans or in moving traits into soybean germplasm. Other breeding methods are known and are described in various plant breeding or soybean textbooks.

When a soybean variety is being employed to develop a new soybean variety or an improved variety the selection methods may include backcrossing, pedigree breeding, recurrent selection, marker assisted selection, modified selection and mass selection or a combination of these methods. The efficiency of the breeding procedure along with the goal of the breeding are the factors for determining which selection techniques are employed. A breeder continuously evaluates the success of the breeding program and therefore the efficiency of any breeding procedures. The success is usually measured by yield increase, commercial appeal and environmental adaptability of the developed germplasm.

The development of new soybean cultivars most often requires the development of hybrid crosses (some exceptions being initial development of mutants directly through the use of the mutating agent, certain materials introgressed by markers, or transformants made directly through transformation methods) and the selection of progeny. Hybrids can be achieved by manual manipulation of the sexual organs of the soybean or by the use of male sterility systems. Breeders often try to identify true hybrids by a readily identifiable trait or the visual differences between Inbred and hybrid material. These heterozygous hybrids are then selected and repeatedly selfed and reselected to form new homozygous soybean lines.

Mass and recurrent selection can be used to improve populations. Several parents are intercrossed and plants are selected based on selected characteristics like superior yield or excellent progeny resistance. Outcrossing to a number of different parents creates fairly heterozygous breeding populations.

Pedigree breeding is commonly used with two parents that possess favorable, complementary traits. The parents are crossed to form a F1 hybrid. The progeny of the F1 hybrid is selected and the best individual F2s are selected; this selection process is repeated in the F3 and F4 generations. The inbreeding is carried forward and approximately F5-F7 the best lines are selected and tested in the development stage for potential usefulness in a selected geographic area.

In backcross breeding a genetic allele or loci is often transferred into a desirable homozygous recurrent parent. The trait from the donor parent and is tracked into the recurrent parent. The resultant plant is bred to be like the recurrent parent with the new desired allele or loci.

The single-seed descent method involves use of a segregating plant population for harvest of one seed per plant. Each seed sample is planted and the next generation is formed. When the F2 lines are advanced to approximately F6 or so, each plant will be derived from a different F2. The population will decline due to failure of some seeds, so not all F2 plants will be represented in the progeny.

New varieties must be tested thoroughly to compare their development with commercially available soybeans. This testing usually requires at least two years and up to six years of comparisons with other commercial soybeans. Varieties that lack the entire desirable package of traits can be used as parents in new populations for further selection or are simply discarded. The breeding and associated testing process is 8 to 12 years' of work prior to development of a new variety. Thousands of varietal lines are produced but only a few lines are selected in each step of the process. Thus the breeding system is like a funnel with numerous lines and selections in the first few years and fewer and fewer lines in the middle years until one line is selected for the final development testing.

The selected line or variety will be evaluated for its growth, development and yield. These traits of a soybean are a result of the variety's genetic potential interacting with its environment. All varieties have a maximum yield potential that is predetermined by its genetics. This hypothetical potential for yield is only obtained when the environmental conditions are near perfect. Since perfect growth conditions do not exist, field experimentation is necessary to provide the environmental influence and to measure its effect on the development and yield of the soybean. The breeder attempts to select for an elevated soybean yield potential under a number of different environmental conditions.

Selecting for good soybean yield potential in different environmental conditions is a process that requires planning based on the analysis of data in a number of seasons. Identification of the varieties carrying a superior combination of traits, which will give consistent yield potential, is a complex science. The desirable genotypic traits in the variety can often be masked by other plant traits, unusual weather patterns, diseases, and insect damage. One widely employed method of identifying a superior plant with such genotypic traits is to observe its performance relative to commercial and experimental plants in replicated studies. These types of studies give more certainty to the genetic potential and usefulness of the plant across a number of environments.

In summary, the goal of the soybean plant breeder is to produce new and unique soybeans and progeny of the soybeans for farmers' commercial crop production. To accomplish this, the plant breeder painstakingly crosses two or more varieties or germplasm. Then the results of this cross are repeatedly selfed or backcrossed to produce new genetic patterns. Newer avenues for producing new and unique genetic alleles in soybeans include introducing (or creating) mutations or transgenes into the genetic material of the soybean are now in practice in the breeding industry. These genetic alleles can alter pest resistance such as disease resistance, insect resistance, nematode resistance, herbicide resistance, or they can alter the plant's environmental tolerances, or its seeds fatty acid compositions, the amount of oil produced, and/or the amino acid/protein compositions of the soybean plant or its seed.

The traits a breeder selects for when developing new soybeans are driven by the ultimate goal of the end user of the product. Thus if the goal of the end user is to resist a certain plant disease so overall more yield is achieved, then the breeder drives the introduction of genetic alleles and their selection based on disease resistant levels shown by the plant. On the other hand, if the goal is to produce specific fatty acid composition, with for example a high level of oleic acid and/or a lower level of linolenic acid, then the breeder may drive the selection of genetic alleles/genes based on inclusion of mutations or transgenes that alter the levels of fatty acids in the seed. Reaching this goal may allow for the acceptance of some lesser yield potential or other less desirable agronomic trait.

The new genetic alleles being introduced in to soybeans are widening the potential uses and markets for the various products and by-products of the oil from the seed plants such as soybean. A major product extracted from soybeans is the oil in the seed. Soybean oil is employed in a number of retail products such as cooking oil, baked goods, margarines and the like. Another useful product is soybean meal, which is a component of many foods and animal feedstuffs.

SUMMARY OF THE INVENTION

One embodiment of the invention relates to seed of a soybean cultivar designated S06-02JR409114. The invention relates to the plant from the seed designated S06-02JR409114, or the plant parts. The invention also encompasses a tissue culture of regenerable cells, cells or protoplasts being from a tissue selected from the group consisting of: leaves, pollen, embryos, meristematic cells, roots, root tips, anthers, flowers, ovule, seeds, stems, pods, petals and the cells thereof.

The invention in one aspect covers a soybean plant, or parts thereof, having all of the physiological and morphological characteristics of the soybean plant.

Another aspect of this invention is the soybean plant seed or derived progeny which contains a transgene which provides herbicide resistance, insect resistance, resistance to disease, resistance to nematodes, male sterility, or which alters the oil profiles, the fatty acid profiles, the amino acids profiles or other nutritional qualities of the seed.

The present invention further covers a method for producing a soybean seed with the steps of crossing at least two parent soybean plants and harvesting the hybrid soybean seed, wherein at least one parent soybean plant is the present invention. In another aspect of the invention covers the hybrid soybean seed and the progeny soybean plant and resultant seed, or parts thereof from the hybrid seed or plant or its progeny.

In an additional aspect, the invention covers a method for producing a soybean progeny from the invention by crossing soybean line S06-02JR409114 with a second soybean plant to yield progeny soybean seed and then growing progeny soybean seed to develop a derived soybean line.

Yet another aspect of the invention covers a method for a breeding program using plant breeding techniques which employ the soybean plant S06-02JR409114 as plant breeding material and performing breeding by selection techniques, backcrossing, pedigree breeding, marker enhanced selection, mutation and transformation.

DETAILED DESCRIPTION

Figure 1:
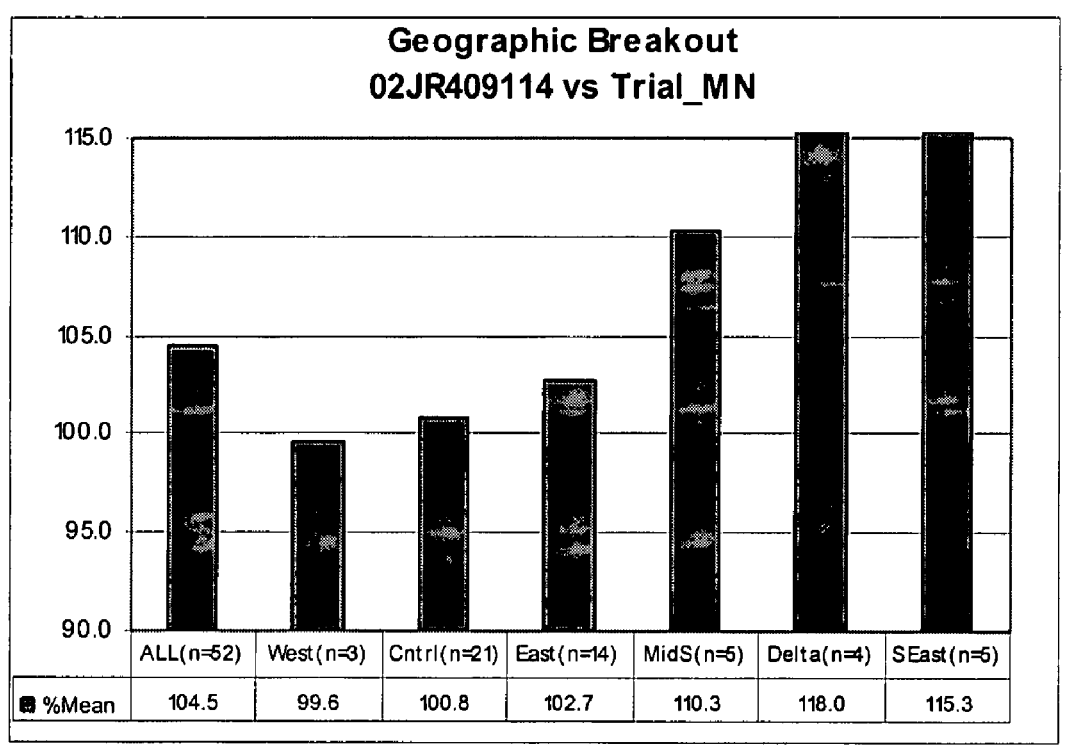
FIG. 1 shows the Geographic Segment Chart—GSEGC shows the breakout for grain yield at standard moisture for S06-02JR409114 across geographic locations.

The following data is used to describe and enable the present soybean invention.

| Trait Code | Performance Trait Description |
|---|---|
| VHNO | Variety/Hybrid Number |
| YGSMN | Grain Yield at Std MST-YGSMN |
| MRTYN | Maturity Days from planting MRTYN |
| HLDGR | Harvest Lodging HLDGR |
| PLHTN | Plant Height (cm) |
| PRR_R | Phytophthora Root Rot Tol PRR_R |
| IC_R | Iron Chlorosis IC_R |
| SDS_R | Sudden Death Syndrome SDS_R |
| SCL_R | Sclerotinia White Mold SCL_R |
| FELSR | Frogeye Leaf Spot FELSR |
| STR_R | Shattering STR_R |
| GLDGR | Green Lodging GLDGR |
| PLBRR | Plant Branching PLBRR |
| EMRGR | Emergence EMRGR |

Syngenta Soybean Data Collection Traits and Timing

| Order | Trait Group | Code | Description | Timing | Comments | # Loc Stage 4 | # Loc Stage 5 | # Loc Stage 6 | Scale |
|---|---|---|---|---|---|---|---|---|---|
| 1 | HS | RRG_R | Presence of RR gene | V2-V4, 4-7 DAYS AFTER SPRAYING | | Home Loc's | Home Loc's | Home Loc's | Roundup 1 = R, 5 = seg, 9 = susc, |
| 1 | HS | RUR_R | Roundup Tolerance Yellowing | R1-R2 | | Home Loc's | Home Loc's | Home Loc's | 1-9 scale, 1 = no yellowing, 9 is extreme yellowing |
| 1 | OTH | EMRGR | Emergence - stand establishment, uniformity and vigor | VE-V3 | NK EPA_R = V2-V6, 2006 on use EMRGR | | 2 | 4 | 1 to 9 (1 = best) |
| 2 | DIS | IC_R | Iron Deficiency Chlorosis | August | Internal Field Nursery | MGOO-2L | MGOO-4.9 | MGOO-4.9 | 1 to 9 (1 = best) |
| 2 | DIS | ICFLR | Iron Deficiency Chlorosis Yellow Flash | Initial flash V2 June-July | Internal Field Nursery | MGOO-2L | MGOO-4.9 | MGOO-4.9 | 1 to 9 (1 = best) |
| 2 | DIS | ICR_R | Iron Deficiency Chlorosis Recovery, (Stunting and/or Green-up) | 2-3 weeks after ICFLR | Internal Field Nursery | MGOO-2L | MGOO-4.9 | MGOO-4.9 | 1 to 9 (1 = best) |
| 2 | DIS | PRR_R | *Phytophthora* Root Rot Tolerance in pond | Scheduled | Internal Field Nursery | | St. Joe | St. Joe | 1 to 9 (1 = best) for field tolerance |
| 2 | NEM | SCN_R | SCN Field Rating | June | Internal Field Nursery | | Conesville, St. Joe | Conesville, St. Joe | Field = 1-9 (1 best) |
| 3 | AGR | FL_CT | Flower Color | R1 Confirmed | Text for VSR | Home Loc's | Home Loc's | Home Loc's | W = White; P = Purple; Seg = Mix |
| 3 | AGR | FL_CR | Flower Color Rating | R1 Confirmed | Numeric for EDC | Home Loc's | Home Loc's | Home Loc's | 1 = White; 2 = Purple; 9 = Seg |
| 3 | AGR | PLCNR | Plant canopy | July-August (R1-R6) | Growth expressive locations. | | Opportunistic | Opportunistic | 1 to 9, 1 = Slender, 5 = Intermediate, 9 = Bush |
| 3 | DIS | ARSTR | Asian Rust Rating | When differences occur | | Opportunistic | Opportunistic | Opportunistic | 1 to 9 (1 = best) |
| 3 | DIS | BSR_R | Brown Stem Rot | When differences occur | | Opportunistic | Opportunistic | Opportunistic | 1 to 9 (1 = best) |
| 3 | DIS | CR_R | Charcoal Rot | When differences occur | | Opportunistic | Opportunistic | Opportunistic | 1 to 9 (1 = best) |
| 3 | DIS | DPC_R | Stem Canker (Northern) | When differences occur | | Opportunistic | Opportunistic | Opportunistic | 1 to 9 (1 = best) |
| 3 | DIS | DPM_R | Stem Canker (Southern) | When differences occur | | Opportunistic | Opportunistic | Opportunistic | 1 to 9 (1 = best) |
| 3 | DIS | FELSR | Frogeye Leaf Spot | When differences occur | | Opportunistic | Opportunistic | Opportunistic | 1 to 9 (1 = best) |
| 3 | DIS | SCL_R | *Sclerotinia* White Mold | When differences occur | | Opportunistic | Opportunistic | Opportunistic | 1 to 9 (1 = best) |
| 3 | DIS | SDS_R | Sudden Death Syndrome | When differences occur | | Opportunistic | Opportunistic | Opportunistic | 1 to 9 (1 = best) |
| 3 | PERF | GLDGR | Green lodging | R5 to R6 | Where differences occur | Opportunistic | Opportunistic | Opportunistic | 1 to 9 (1 best) 1 = All erect; 5 = 45 degrees; 9 = flat |
| 4 | AGR | MRTYD | Maturity Date (MMDD) - 95% of plants in row have mature pod color | R8 | Home locations + 1-2 off site/station | ~1-2 | ~5 | ~10 | MMDD (Sep. 10 = 0910) |
| 4 | AGR | HILCT | Hilum Color | R8 | Text | Home Loc's | Home Loc's | Home Loc's | G = Gray, BR = Brown, BF = Buff; BL = Black; IB = Imperfect Black; Y = Yellow; IY = Imperfect |

-continued

Syngenta Soybean Data Collection Traits and Timing

| Order | Trait Group | Code | Description | Timing | Comments | # Loc Stage 4 | # Loc Stage 5 | # Loc Stage 6 | Scale |
|---|---|---|---|---|---|---|---|---|---|
| 4 | AGR | PB_CR | Pubescence Color | R8-Harvest | Numeric for EDC | Home Loc's | Home Loc's | Home Loc's | Yellow; Seg = Mix 1 = Gray; 2 = Tawny; 4 = Lt. Tawny; 9 = Seg |
| 4 | AGR | PB_CT | Pubescence Color | R8-Harvest | Text for VSR | Home Loc's | Home Loc's | Home Loc's | G = Gray; T = Tawny; LT = Lt. Tawny; Seg = Mix |
| 4 | AGR | PD_CR | Pod Color | R8-Harvest | Numeric for EDC | Home Loc's | Home Loc's | Home Loc's | 1 = Tan; 2 = Brown; 9 = Seg |
| 4 | AGR | PD_CT | Pod Color | R8-Harvest | Text for VSR | Home Loc's | Home Loc's | Home Loc's | T = Tan; B = Brown; Seg = Mix |
| 4 | AGR | PLBRR | Plant branching | R8-Harvest | Growth expressive locations. | Optional | Home Loc's | Home Loc's | 1 to 9, 1 = no branching; 5 = average branching; 9 = profuse branching |
| 4 | AGR | PLHTN | Plant Height (cm) | Harvest | Growth expressive locations. | Optional | Home Loc's | Home Loc's | Taken in cm |
| 4 | DIS | GS_R | Green Stem | Harvest | Where differences occur | Opportunistic | Opportunistic | Opportunistic | 1 to 9 (1 = best) |
| 4 | PERF | HLDGR | Harvest Lodging | R8 - Harvest | Where differences occur | Opportunistic | Opportunistic | Opportunistic | 1 to 9 (1 best) 1 = All erect; 5 = 45 degrees; 9 = flat |
| 4 | PERF | HVAPR | Harvest Appearance | Harvest | Where differences occur | Opportunistic | Opportunistic | Opportunistic | 1 to 9, 1 = Excellent, 5 = Avg, 9 = Poor |
| 4 | PERF | STR_R | Shattering | Harvest | Hill plot planter, 2006? | | Opportunistic + Bay and St Joe | Opportunistic + Bay and St. Joe | 1 to 9 (1 = best) |

Roundup is a trademark of Monsanto
Order 1 = Seedling, 2 = Vegetative, 3 = Reproductive to grain-fill, 4 = Maturity
Opportunistic ratings should only be collected if differences occur.
At least one variety has a rating of 5 or greater and there is a spread of 3 in the ratings.
Trait Definitions
Opportunistic Ratings developed in YT. Opportunistic ratings should only be collected if differences occur. At least one variety has a rating of 5 or greater and there is a spread of 3 in the ratings. (Scale 1-9, 1 = Best).
Emergence (EMRGR) A rating of the uniform establishment and growth of seedlings. Taken from V1-V3, (Scale 1-9).
Maturity (MRTYD) The month and day (MMDD) when 95% of the main stem pods in the plot have reached their mature color.
Plant Height (PLHTN) The average measured plant height in cm.
Branching (PLBRR) Rating of the number of branches and their relative importance to yield. Taken at growth expressive locations. (Scale: 1-9, 1 = stick, no branching, 3 = 1 seed bearing branch, 5 = average branching or 2-3 seed bearing branches, 7 = 3-4 seed bearing branches. 9 = profuse branching).
Green Lodging (GLDGR) Rating based on the average of plants leaning from vertical in R5 to R6 stage (Scale 1-9, 1 to 9 (1 best) 1 = All erect; 5 = 45 degrees; 9 = flat).
Harvest Lodging (HLDGR) Rating based on the average of plants leaning from vertical at harvest (scale 1-9, 1 to 9 (1 best) 1 = All erect; 5 = 45 degrees; 9 = flat).
Shatter (STR_R) Rating of pre-harvest loses based on amount of plants with open pods (Scale 1-9).
Iron Deficiency Chlorosis (IC_R) final rating = average of initial Yellow Flash (ICFLR) and recovery (ICR_R) taken 2-3 weeks after initial yellow flash. (Scale 1-9, 1 = Best). LS means analysis unequal entries and reps between years.
Soybean Cyst Nematode (CN_1R, CN_3R, CN_5R, CN14R) Greenhouse screen-30 day screen using infested soil. Rating Scale based upon female reproduction index on a susceptible check set where <10% = R; <30% = MR; <60% = MS; >60% = S. In priority order, the races screened include: 3, 14, 1 & 5.
*Phytophthora* Root Rot Field tolerance (PRR_R) or actual gene (RPS_T).
Sudden Death Syndrome (SDS_R) based on leaf area affected, scale 1-9. Can be GH or field.
Brown Stem Rot (BSR_R) Greenhouse pot-root dip or field rating of leaf symptoms. (Scale 1-9)
Root Knot Nematode *Arenaria* (MA_R), *Incognita* (MI_R), *Javanica* (MJ_R) RKN). Scale 1-9.
Stem Canker North (DPM_R) Southern (DPM_R). Scale 1-9.
Sulfentrazone (SUL_R) Greenhouse nursery rating damage of multiple rates. Scale 1-9.
Metributzin (MET_R) Greenhouse nursery rating damage of multiple rates. Scale 1-9.
Hypocotyl Elongation (HYP_R) A rating of a variety's hypocotyl extension after germination when planted at a 5" depth in sand and maintained a warm germination environment for 10 days. (Scale 1 = Long, 5 = Intermediate, 9 = Short)

TRAIT DEFINITIONS

Hypocotyl Elongation (HYPO) A rating of a variety's hypocotyl extension after germination when planted at a 5" depth in sand and maintained a warm germination environment for 10 days.

Seedling Establishment (EMG) A rating of the uniform establishment and growth of seedlings.

Peroxidase Activity (Perox)—seed protein peroxidase activity is defined as a chemical taxonomic technique to separate cultivars based on the presence or absence of the peroxidase enzyme in the seed coat. Ratings are POS=positive for peroxidase enzyme or NEG=negative for peroxidase enzyme.

Plant Height (PLTHT) The average measured plant height in centimeters.

Branching (BRANCH) Rating of the number of branches and their relative importance to yield. This rating is taken at growth expressive locations.

Green Lodging (GLODGE) Rating based on the average of plants leaning from vertical in R5 to R6 stage prior to maturity.

Harvest Lodging (LODGE) Rating based on the average of plants leaning from vertical at harvest. Lodging score (1=completely upright, 9=completely prostrate), Phytophthora Root Rot (PGR) or (PFT) Greenhouse pot-root dip method for PFT and hypodermic needle method for rating PGR.

Root Knot Nematode (RKN) Greenhouse screen—45 day screen root inoculated with eggs and juveniles. Rating Scale based upon female reproduction index on a susceptible check set determined by number of galls present.

Stem Canker (STC) Based on number of lesions, scale 1-5.

Sulfentrazone (SULF) Authority™ (commercial herbicide) Greenhouse nursery rating damage of multiple rates.

Metributzin (MET) Greenhouse nursery rating damage of multiple rates.

Brown Stem Rot (BSR or BSR_R) This disease is caused by the fungus *Phialophora gregata*. The disease is a late-season, cool-temperature, soil borne fungus which in appropriate favorable weather can cause up to 30 percent yield losses in soybean fields. BSR information is gathered in a greenhouse with a plant in a pot then a root dip procedure is employed. BSR_R is an opportunistic field rating scale is 1-9.

Sudden Death Syndrome (SDS or SDS_R) This disease is caused by slow-growing strains of *Fursarium solani* that produce bluish pigments in culture. The disease is a mid to late season, soil borne disease that occurs in soybean fields with high yield potential. Yield losses may be total or severe in infected fields. Sudden Death Syndrome (SDS_R) is based on leaf area affected. The scale used for these tests is 1-5 or if identified as SDS_R the scale is 1-9.

*Sclerotinia* White Mold (SCL_R) This disease is caused by the fungal pathogen *Sclerotinia sclerotium*. The fungus can overwinter in the soil for many years as sclerotia and infecting plants in prolonged periods of high humidity or rainfall. Yield losses may be total or severe in infected fields. *Sclerotinia* White Mold (SCL_R) rating is a field rating (1-9 scale) based the percentage of wilting of dead plants in a plot.

Frog Eye Leaf Spot (FELSR) This is caused by the fungal pathogen *Cercospora sojina*. The fungus survives as mycelium in infected seeds and in infested debris. With adequate moisture new leaves become infected as they develop until all the leaves are infected. Yield losses may be up to 15% in severe infected fields. Frog Eye Leaf Spot (FELSR) rating is a field rating (1-9 scale) based the percentage of leaf area affected.

Soybean Cyst Nematode (SCN) The Soybean Cyst Nematode Heterodera glycines, is a small plant-parasitic roundworm that attacks the roots of soybeans. Soybean Cyst Nematode (SCN) for purposes of these tests is done as a greenhouse screen—30 day screen using infested soil. The rating scale is based upon female reproduction index on a susceptible check set where <10%=R (RESISTANT); <30%=MR (MODERATELY RESISTANT); <60%=MS (MODERATELY SUSPECTIBLE); >60%=S (SUSPECTIBLE). In priority order, the screening races include: 3, 14, & 1.

Maturity Date (MAT or MRTYN) Plants are considered mature when 95% of the pods have reached their mature color. For MAT, the number of days is calculated from August 31 or MRTYN is calculated from the number of days from planting date.

Relative Maturity Group (RM) Industry Standard for varieties groups, based day length or latitude. Long day length (northern areas in the Northern Hemisphere) is classified as (Groups 000, 00, 0,). Mid day lengths variety groups lie in the middle (Groups I-VI). Very short day lengths variety groups (southern areas in Northern Hemisphere) are classified as (Groups VII, VIII, IX).

Seed Yield (YSGMN) The actual grain yield at harvest reported in the unit's bushels/acre.

Shattering (SHAT or STR_R) The rate of pod dehiscence prior to harvest. Pod dehiscence is the process of beans dropping out of the pods. Shatter (SHAT) for these tests the rating of pre-harvest loses is based on amount of plants with open pods on a scale of 1-5, STR_R on a scale 1-9.

Plant Means the plant, in any of its stages of life including the seed or the embryo, the cotyledon, the plantlet, the immature or the mature plant, and plant parts.

Plant Parts Means the anthers, pollen, nodes, roots, flowers, petals, seeds, pods, leaves, stems, and cells (but only to the extent the genetic makeup of the cell has paternal and maternal) and the like.

Palmitic Acid Means a fatty acid, $C_{15}H_{31}COOH$, occurring in soybean. This is one of the five principal fatty acids of soybean oil.

Linolenic Acid Means an unsaturated fatty acid, $C_{17}H_{29}COOH$, occurring in soybean. This is one of the five principal fatty acids of soybean oil.

Stearic Acid Means a colorless, odorless, waxlike fatty acid, $CH_3(CH_2)_{16}COOH$, occurring in soybean. This is one of the five principal fatty acids of soybean oil.

Oleic Acid Means an oily liquid fatty acid, $C_{17}H_{33}COOH$, occurring in soybean. This is one of the five principal fatty acids of soybean oil.

Linoleic Acid Means an unsaturated fatty acid, $C_{17}H_{31}COOH$, occurring in soybean. This is one of the five principal fatty acids of soybean oil.

DEFINITIONS OF STAGING OF DEVELOPMENT

The plant development staging system employed in the testing of this invention divides stages as vegetative (V) and reproductive (R). This system accurately identifies the stages of any soybean plant. However, all plants in a given field will not be in the stage at the same time. Therefore, each specific V or R stage is defined as existing when 50% or more of the plants in the field are in or beyond that stage.

The first two stages of V are designated a VE (emergence) and VC (cotyledon stage). Subdivisions of the V stages are then designated numerically as V1, V2, V3 through V (n). The last V stage is designated as V (n), where (n) represents the number for the last node stage of the specific variety. The (n) will vary with variety and environment. The eight subdivisions of the reproductive stages (R) states are also designated numerically. R1=beginning bloom; R2=full bloom; R3=beginning pod; R4=full pod; R5=beginning seed; R6=full seed; R7=beginning maturity; R8=full maturity.

Soybean Cultivar S06-02JR409114

The present invention is S06-02JR409114 is a mid Maturity Group IV soybean cultivar. This cultivar is developed to be sold commercially in the Midsouth, Delta and Southeast where other mid Maturity Group IV soybeans are grown, especially where there is infestation by Soybean Cyst Nematode and Frogeye Leafspot.

This soybean variety in one embodiment carries one or more transgenes, for example, the glyphosate tolerance transgene, a desaturase gene or other transgenes. In another embodiment of the invention does not carry any herbicide resistance traits. In yet another embodiment of the invention, the soybean does not carry any transgenes but carries alleles for aphid resistance, cyst nematode resistance and/or brown stem rot or the like.

The traits of the invention are listed below.

Traits

| Plant Characteristics | |
|---|---|
| Glyphosate resistant trait-RR ® | Y |
| STS ® | N |
| Flower Color | W |
| Pubescence Color | LT |
| Pod Color | B |
| Hilum Color | BL |
| % Protein 13% mst. | 34.5 |
| % Oil @13% mst. | 18.1 |
| Seed Size/Lb | 2700 |
| Stem Termination | INDET |

| Plant Health | |
|---|---|
| Rps Gene | 1c |
| SCN RACE 1 FI % | |
| SCN RACE 3 FI % | 4.0 |
| SCN RACE 5 FI % | |
| SCN RACE 14 FI % | 5.0 |
| SCN Source | 88788 |
| Root Knot Nematode-Incognita | |
| Root Knot Nematode-Arenaria | |
| Stem Canker (Southern) | 1.0 |
| Stem Canker Tolerance (Southern) | |
| Chloride Sensitivity | |

Rps gene indicates the specific gene for resistance but if none are indicated then none are known to be present
Y = Yes, has trait. N = no does not contain trait
SCN = Soybean Cyst Nematode
RoundUp Ready ®, Roundup ® and Roundup ® Ultra are trademarks of Monsanto Company. STS ® is a trademark of DuPont.
Ratings are on a 1 to 9 scale with 1 being the best.

Additional Traits

| Descriptive Traits | |
|---|---|
| Flower Color: | White |
| Pubescence Color: | Light Tawny |
| Pod Color: | Brown |
| Hilum Color: | Black |
| Leaf Shape: | Ovate |
| Stem Termination: | Indeterminate |
| Seed Coat Color: | Yellow |
| Hypocotyl Color: | Green with Bronze Band |
| Maturity Group | 4 |
| Relative Maturity | 4-6 |
| Performance Traits | |
| Phytophthora Genes | Rps1c |
| Hypocotyl Length | Long |
| Frogeye Leafspot | Mod. Resist. |
| Soybean Cyst Nematode | R 3,14 |

The present invention provides methods and composition relating to plants, seeds and derivatives of the soybean cultivar S06-02JR409114. Soybean cultivar S06-02JR409114 has superior characteristics. The S06-02JR409114 line has been selfed sufficient number of generations to provide a stable and uniform plant variety.

Cultivar S06-02JR409114 shows no variants other than expected due to environment or that normally would occur for almost any characteristic during the course of repeated sexual reproduction. Some of the criteria used to select in various generations include: seed yield, emergence, appearance, disease tolerance, maturity, plant height, and shattering data.

The inventor believes that S06-02JR409114 is similar to the comparison varieties. However, as shown in the tables, S06-02JR409114 differs from these cultivars.

Direct comparisons were made between S06-02JR409114 and the listed commercial varieties. Traits measured included yield, maturity, lodging, plant height, branching, field emergence, and shatter. The results of the comparison are presented in below.

The number of tests in which the varieties were compared is shown with the environments, mean and standard deviation for some traits.

The present invention S06-02JR409114 can carry genetic engineered recombinant genetic material to give improved traits or qualities to the soybean. For example, but not limited to, the present invention can carry the glyphosate resistance gene for herbicide resistance as taught in the Monsanto patents (WO92/00377, WO92/04449, U.S. Pat. No. 5,188,642 and U.S. Pat. No. 5,312,910) or STS mutation for herbicide resistance. Additional traits carried in transgenes or mutation can be transferred into the present invention. Some of these genes include genes that give disease resistance to *sclerotinia* such as the oxalate oxidase (Ox Ox) gene as taught in PCT/FR92/00195 Rhone Polunc and/or an Oxalate Decarboxylase gene for disease resistance or genes designed to alter the soybean oil within the seed such as desaturase, thioesterase genes (shown in EP0472722, U.S. Pat. No. 5,344,771) or genes designed to alter the soybean's amino acid characteristics. This line can be crossed with another soybean line which carries a gene that acts to provide herbicide resistance or alter the saturated and/or unsaturated fatty acid content of the oil within the seed, or the amino acid profile of the seed.

The present invention S06-02JR409114 is employed in a number of plot repetitions to establish trait characteristics.

Geographic Summary

The target variety yield is given as a percent of the trial average at all locations shown in FIG. 1 and each geographic segment West to East or Central (Cntrl) to South East where there are three or more locations. The plots for these trials are two row 17.5 foot plots planted in 30-inch row spacing. The plants in the plots are a combination of experimental material and commercial material. There are usually 36 varieties and there are approximately 300 plants of each variety with two replications in about 20-25 locations. The data shown in FIG. 1 is only charted if there are at least 3 or more locations.

The present invention differs from the mean of the comparison commercial and experimental soybean lines in that the present soybean cultivar is across 52 locations, meeting and exceeding the mean yield of the group of soybeans (GRP_MN) that were tested and displayed in this geographic segment chart (GSEGC). In the Southern regions (Mid South, Delta and Southeast) the present invention has an exceptional yield advantage, yielding about 10.3-18.0% above the group mean in these regions as shown in FIG. 1. In the West and Central regions, yields similar to the Group Mean yields in these regions.

Figure 2:
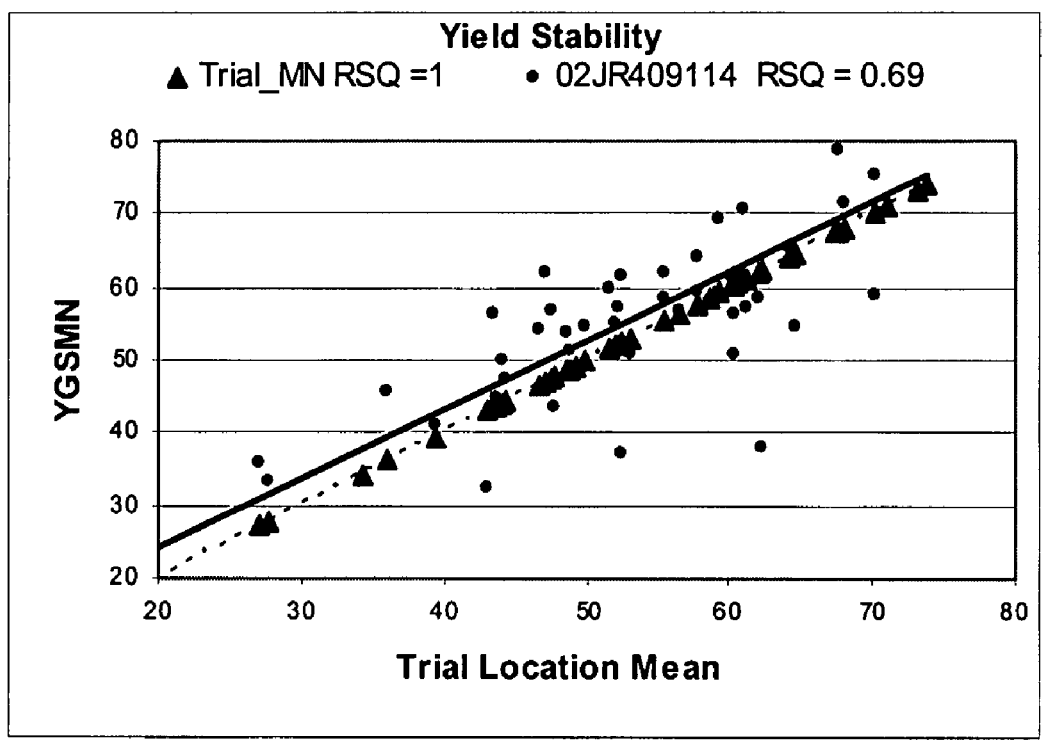
FIG. 2 shows the Group Mean chart (GRP_MN=Group Mean) of Grain Yield at standard moisture for S06-02JR409114. This chart shows Yield Stability–Win>5% of trial mean, Tie + or −5% of trial mean, Loses<5% of trial mean. The chart's vertical axis=yield of target variety, its horizontal axis=location average yield. When the target variety line is above the location average line this is desirable. The RSQ of the target variety shows a number. This number when it is closest to 1=yield stability.

The present invention S06-02JR409114 is employed in a trial with a number of environments. The results of the grain yield at standard moisture are shown in FIG. 2. The present invention is a variety that will yield at the mean or slightly above in the low yielding environments. If the environment is extremely high yielding the present invention tends to perform well when compared to the group mean. At about the 40-70 bushels per acre range the present invention starts to accelerate its yield and exceeds the level of the group mean. There are a number of low outlier results in this range which makes the yield stability of the present invention less than the group mean stability in these locations. These tests allow the usefulness of the invention to be shown in light of the environmental genetic interactions.

type and for understanding the pedigree of the present invention and identifying plants that have the present invention as an ancestor; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

Additionally, these markers such as SSRs, RFLP's, SNPs, Ests, AFLPs, gene primers, and the like can be developed and employed to identify genetic alleles which have an association with a desired trait. The allele can be used in a marker assisted breeding program to move traits (native, normative (from a different species, or transgenes) into the present invention. The value of markers includes allowing the intro- Research Data Yield Performance Chart

| VHNO | YGSMN | MRTYN | HLDGR | PLHTN | PRR_R | IC_R | SDS_R | FELSR | GS_R | STR_R | GLDGR | EMRGR | TESTP |
|---|---|---|---|---|---|---|---|---|---|---|---|---|---|
| 4212RR/STS/N | 56.2 | 140.7 | 2.8 | 88.8 | 3.2 | 4.8 | 3.3 | 2.0 | 3.3 | 2.2 | 2.9 | 2.7 | 104.0 |
| 02JR409114 | 56.0 | 143.7 | 3.8 | 106.7 | 3.6 | 7.8 | 5.5 | 3.0 | 5.3 | 1.8 | 4.0 | 2.8 | 105.3 |
| 4512RR/N | 54.9 | 143.2 | 3.6 | 101.3 | 3.5 | 7.3 | 3.0 | 6.5 | 4.5 | 1.7 | 4.1 | 3.3 | 102.5 |
| AG3905 | 53.6 | 138.4 | 3.4 | 94.2 | 3.6 | 5.9 | 3.6 | 6.5 | 3.5 | 2.8 | 4.6 | 3.0 | 99.6 |
| 94B13 | 53.2 | 138.3 | 3.9 | 97.3 | 3.4 | 6.2 | 4.1 | 2.8 | 3.3 | 3.2 | 5.7 | 2.9 | 99.2 |
| S43-B1 | 52.9 | 140.4 | 4.2 | 96.3 | 3.1 | 4.9 | 3.1 | 3.3 | 4.3 | 2.2 | 5.1 | 2.9 | 99.2 |
| S44-J5 | 52.6 | 141.5 | 3.6 | 99.2 | 3.7 | 6.6 | 2.9 | 3.0 | 4.7 | 2.5 | 4.2 | 3.1 | 97.4 |
| S41-M5 | 52.1 | 138.5 | 4.7 | 98.6 | 4.7 | 5.6 | 4.6 | 1.3 | 3.3 | 1.7 | 6.0 | 3.0 | 96.2 |
| Environments | 54.0 | 21.0 | 26.0 | 29.0 | 2.0 | 3.0 | 9.0 | 2.0 | 4.0 | 3.0 | 3.0 | 26.0 | 52.0 |
| Grand Mean | 54.4 | 141.6 | 3.7 | 98.0 | 3.6 | 6.4 | 3.7 | 4.6 | 4.3 | 2.2 | 4.3 | 3.1 | 101.3 |
| Check Mean | 53.6 | 140.1 | 3.7 | 96.5 | 3.6 | 5.9 | 3.5 | 3.6 | 3.9 | 2.3 | 4.7 | 3.0 | 99.7 |
| LSD (0.05) | 2.0 | 1.1 | 0.4 | 2.6 | 0.0 | 1.4 | 0.9 | 1.3 | 1.7 | 0.0 | 0.8 | 0.3 | 0.0 |

Each of these lines has their own positive traits. Each of these lines is different from the present invention. The present invention has a higher rating for Sudden Death Syndrome (low ratings are preferred) than does the mean for the commercial lines to which it is compared. The present invention has a significantly better rating for the agronomic trait of shatter at 1.8 than the grand mean at 2.2 or the check mean at 2.3 for the tested material. The yield and other data is a snapshot of each of these lines' results across the specific environments and will differ when other environmental interactions are measured.

This invention also is directed to methods for producing a new soybean plant by crossing a first parent plant with a second parent plant wherein the first or second parent plant is the present invention. Additionally, the present invention may be used in the variety development process to derive progeny in a breeding population or crossing. Further, both first and second parent plants can be or be derived from the soybean line S06-02JR409114. A variety of breeding methods can be selected depending on the mode of reproduction, the trait, the condition of the germplasm. Thus, any such methods using the S06-02JR409114 are part of this invention: selfing, backcrosses, recurrent selection, mass selection and the like.

The scope of the present invention includes use of marker methods. In addition to phenotypic observations, the genotype of a plant can also be examined. There are many techniques or methods known in that which are available for the analysis, comparison and characterization of plant's genogression of the allele(s)/trait(s) into the desired germplasm with little to no superfluous germplasm being dragged from the allele/trait donor plant into the present invention. This results in formation of the present invention for example, cyst nematode resistance, brown stem rot resistance, aphid resistance, Phytophthora resistance, IDC resistance, BT genes, male sterility genes, glyphosate tolerance genes or drought tolerance genes.

Many traits have been identified that are not regularly selected for in the development of a new cultivar. Using materials and methods well known to those persons skilled in the art, traits that are capable of being transferred, to cultivar of the present invention include, but are not limited to, herbicide tolerance, resistance for bacterial, fungal, or viral disease, nematode resistance, insect resistance, enhanced nutritional quality, such as oil, starch and protein content or quality, improved performance in an industrial process, altered reproductive capability, such as male sterility or male/female fertility, yield stability and yield enhancement. Other traits include the production of commercially valuable enzymes or metabolites within the present invention.

Transgenes maybe directly introduced into the cultivar using genetic engineering and transformation techniques well known in the art or introduced into the cultivar through a process which uses a donor parent which has the transgene(s) already introgressed. This process of introduction of a transgene(s) or native/non-native traits into the cultivar may use the donor parent in a marker assisted trait conversion process, where the trait may be moved for example by backcrossing using the markers for selection of subsequent generations.

The laboratory-based techniques described above, in particular RFLP and SSR, can be used in such backcrosses to identify the progenies having the highest degree of genetic identity with the recurrent parent. This permits one to accelerate the production of soybean cultivars having at least 90%, 95%, 99% genetic, or genetically identical to the recurrent parent, and further comprising the trait(s) introgressed from the donor patent. Such determination of genetic identity can be based on markers used in the laboratory-based techniques described above.

The last backcross generation is then selfed to give pure breeding progeny for the gene(s) being transferred. The resulting plants have essentially all of the morphological and physiological characteristics of cultivar of the present invention, in addition to the gene trait(s) transferred to the inbred. The exact backcrossing protocol will depend on the trait being altered to determine an appropriate testing protocol. Although backcrossing methods are simplified when the trait being transferred is a dominant allele, a recessive allele may also be transferred. In this instance it may be necessary to introduce a test of the progeny to determine if the desired trait has been successfully transferred.

The cultivar of the invention can also be used for transformation where exogenous genes are introduced and expressed by the cultivar of the invention. Genetic variants created either through traditional breeding methods using cultivar of the present invention or through transformation of such cultivar by any of a number of protocols known to those of skill in the art are intended to be within the scope of this invention (see e.g. Trick et al. (1997) Recent Advances in Soybean Transformation, Plant Tissue Culture and Biotechnology, 3:9-26).

Transformation methods are means for integrating new genetic coding sequences (transgenes) into the plant's genome by the incorporation of these sequences into a plant through man's assistance. Many dicots including soybeans can easily be transformed with Agrobacterium. Methods of introducing desired recombinant DNA molecule into plant tissue include the direct infection or co-cultivation of plant cells with Agrobacterium tumefaciens, Horsch et al., Science, 227:1229 (1985). Descriptions of Agrobacterium vector systems and methods are shown in Gruber, et al., "Vectors for Plant Transformation, in Methods in Plant Molecular Biology & Biotechnology" in Glich et al., (Eds. pp. 89-119, CRC Press, 1993). Transformed plants obtained via protoplast transformation are also intended to be within the scope of this invention. The most common method of transformation after the use of agrobacterium is referred to as gunning or microprojectile bombardment. This process has small gold-coated particles coated with DNA (including the transgene) shot into the transformable material. Techniques for gunning DNA into cells, tissue, explants, meristems, callus, embryos, and the like are well known in the prior art.

The DNA used for transformation of these plants clearly may be circular, linear, and double or single stranded.

In general, a transgene typically comprises a nucleotide sequence whose expression is responsible or contributes to the trait, under the control of a promoter capable of directing the expression of the nucleotide sequence at the desired time in the desired tissue or part of the plant.

A transgene typically comprises a nucleotide sequence whose expression is responsible or contributes to the trait, under the control of a promoter capable of directing the expression of the nucleotide sequence at the desired time in the desired tissue or part of the plant. Constitutive, tissue-specific or inducible promoters are well known in the art and have different purposes and each could be employed. The transgene(s) may also comprise other regulatory elements such as for example translation enhancers or termination signals. The transgene may be adapted to be transcribed and translated into a protein, or to encode RNA in a sense or antisense orientation such that it is not translated or only partially translated.

Sometime the DNA is in the form of a plasmid. The plasmid may contain additional regulatory and/or targeting sequences which assist the expression or targeting of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense or partial sense: multiple gene copies can be used.

After the transformation of the plant material is complete, the next step is identifying the cells or material, which has been transformed. In some cases, a screenable marker is employed such as the beta-glucuronidase gene of the uidA locus of E. coli. Then, the transformed cells expressing the colored protein are selected for either regeneration or further use. In many cases, a selectable marker identifies the transformed material. The putatively transformed material is exposed to a toxic agent at varying concentrations. The cells not transformed with the selectable marker, which provides resistance to this toxic agent, die. Cells or tissues containing the resistant selectable marker generally proliferate. It has been noted that although selectable markers protect the cells from some of the toxic affects of the herbicide or antibiotic, the cells may still be slightly affected by the toxic agent by having slower growth rates. If the transformed materials are cell lines then these lines are used to regenerate plants. The cells' lines are treated to induce tissue differentiation. Methods of regeneration of plants are well known in the art. General methods of culturing plant tissues are provided for example by Maki et al. "Procedures for Introducing Foreign DNA into Plants" in Methods in Plant Molecular Biology & Biotechnology, Glich et al. (Eds. pp. 67-88 CRC Press, 1993); and by Phillips et al. "Cell-Tissue Culture and In-Vitro Manipulation" in Soybean & Soybean Improvement, 3rd Edition Sprague et al. (Eds. pp. 345-387) American Society of Agronomy Inc. et al. 1988.

The plants from the transformation process or the plants resulting from a cross using a transformed line or the progeny of such plants which carry the transgene are transgenic plants.

The genes responsible for a specific gene trait are generally inherited through the nucleus. Known exceptions are, e.g. the genes for male sterility, some of which are inherited cytoplasmically, but still act as single gene traits. In a preferred embodiment, a transgene to be introgressed into the cultivar S06-02JR409114 is integrated into the nuclear genome of the donor, non-recurrent parent or the transgene is directly transformed into the nuclear genome of cultivar S06-02JR409114. In another embodiment of the invention, a transgene to be introgressed into cultivar S06-02JR409114 is integrated into the plastid genome of the donor, non-recurrent parent or the transgene is directly transformed into the plastid genome of cultivar S06-02JR409114. In a further embodiment of the invention, a plastid transgene comprises gene(s) that have transcribed from a single promoter or two or more genes transcribed from a single promoter.

A non-exclusive list of traits or nucleotide sequences capable of being transferred into cultivar S06-02JR409114, using material and methods well known to those persons skilled in the art are as follows: genetic factor(s) responsible for resistance to brown stem rot (U.S. Pat. No. 5,689,035) or resistance to cyst nematodes (U.S. Pat. No. 5,491,081); a transgene encoding an insecticidal protein, such as, for example, a crystal protein of Bacillus thuringiensis or a vegetative insecticidal protein from Bacillus cereus, such as VIP3 (see, for example, Estruch et al. Nat Biotechnol (1997) 15:137-41; a herbicide tolerance transgene whose expression renders plants tolerant to the herbicide, for example, expression of an altered acetohydroxyacid synthase (AHAS) enzyme confers upon plants tolerance to various imidazolinone or sulfonamide herbicides (U.S. Pat. No. 4,761,373.) Other traits capable of being transformed into cultivar S06-02JR409114 include, for example, a non-transgenic trait conferring to cultivar S06-02JR409114 tolerance to imidazolinones or sulfonylurea herbicides; a transgene encoding a mutant acetolactate synthase (ALS) that renders plants resistant to inhibition by sulfonylurea herbicides (U.S. Pat. No. 5,013,659); a gene encoding a mutant glutamine synthetase (GS) resistant to inhibition by herbicides that are known to inhibit GS, e.g. phosphinothricin and methionine sulfoximine (U.S. Pat. No. 4,975,374); and a Streptomyces bar gene encoding a phosphinothricin acetyl transferase resulting in tolerance to the herbicide phosphinothricin or glufosinate (U.S. Pat. No. 5,489,520.)

Other genes capable of being transferred into the cultivar S06-02JR409114 of the invention include toleration to inhibition by cyclohexanedione and aryloxyphenoxypropanoic acid herbicides (U.S. Pat. No. 5,162,602), which is conferred by an altered acetyl coenzyme A carboxylase (ACCase); transgenic glyphosate tolerant plants, which tolerance is conferred by an altered 5-enolpyruvyl-3-phosphoshikimate (EPSP) synthase gene; tolerance to a protoporphyrinogen oxidase inhibitor, which is achieved by expression of a tolerant protoporphyrinogen oxidase enzyme in plants (U.S. Pat. No. 5,767,373.) In yet another embodiment of the present invention, a transgene transformed or introgressed into cultivar S06-02JR409114 comprises a gene conferring tolerance to a herbicide and at least another nucleotide sequence for another trait, such as for example, insect resistance or tolerance to another herbicide. Another gene capable of being transferred into the cultivar S06-02JR409114 of the invention expresses thioredoxin and thioredoxin reductase enzymes for modifying grain digestibility and nutrient availability (U.S. Pat. Appl. No. 20030145347.)

Direct selection may be applied where the trait acts as a dominant trait. An example of a dominant trait is herbicide tolerance. For this selection process, the progeny of the initial cross are sprayed with the herbicide prior to the backcrossing. The spraying eliminates any plant that does not have the desired herbicide tolerance characteristic, and only those plants that have the herbicide tolerance gene are used in the subsequent backcross. This process is then repeated for the additional backcross generations.

Further reproduction of the cultivar can occur by tissue culture and regeneration. Tissue culture of various tissues of soybeans and regeneration of plants therefrom is well known and widely published. For example, reference may be had to Komatsuda, T. et al., "Genotype X Sucrose Interactions for Somatic Embryogenesis in Soybean," Crop Sci. 31:333-337 (1991); Stephens, P. A. et al., "Agronomic Evaluation of Tissue-Culture-Derived Soybean Plants," Theor. Appl. Genet. (1991) 82:633-635; Komatsuda, T. et al., "Maturation and Germination of Somatic Embryos as Affected by Sucrose and Plant Growth Regulators in Soybeans Glycine gracilis Skvortz and Glycine max (L.) Merr.," Plant Cell, Tissue and Organ Culture, 28:103-113 (1992); Dhir, S. et al., "Regeneration of Fertile Plants from Protoplasts of Soybean (Glycine max L. Merr.): Genotypic Differences in Culture Response," Plant Cell Reports (1992) 11:285-289; Pandey, P. et al., "Plant Regeneration from Leaf and Hypocotyl Explants of Glycine wightii (W. and A.) VERDC. var longicauda," Japan J. Breed. 42:1-5 (1992); and Shetty, K., et al., "Stimulation of In Vitro Shoot Organogenesis in Glycine max (Merrill.) by Allantoin and Amides," Plant Science 81:(1992) 245-251; as well as U.S. Pat. No. 5,024,944, issued Jun. 18, 1991 to Collins et al. and U.S. Pat. No. 5,008,200, issued Apr. 16, 1991 to Ranch et al. Thus, another aspect of this invention is to provide cells that upon growth and differentiation produce soybean plants having all or essentially all the physiological and morphological characteristics of cultivar S06-02JR409114. The disclosures, publications, and patents that are disclosed herein are all hereby incorporated herein in their entirety by reference.

The seed of soybean cultivar S06-02JR409114 further comprising one or more specific, single gene traits, the plant produced from the seed, the hybrid soybean plant produced from the crossing of the cultivar with any other soybean plant, hybrid seed, and various parts of the hybrid soybean plant can be utilized for human food, livestock feed, and as a raw material in industry.

Soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board & American Soybean Association Special Report 92S, May 1990.) Changes in fatty acid composition for improved oxidative stability and nutrition are constantly sought after. (U.S. Pat. No. 5,714,670 Soybeans Having Low Linolenic Acid and Low Palmitic Acid Contents; U.S. Pat. No. 5,763,745 Soybeans having Low Linolenic acid content and Palmitic acid content of at least eleven percent; U.S. Pat. No. 5,714,668 Soybeans Having Low Linolenic Acid And Elevated Stearic Acid Content; U.S. Pat. No. 5,714,669 A17 Soybeans Having Low Linolenic Acid Content and Descendents; U.S. Pat. No. 5,710,369 A16 Soybeans Having Low Linolenic Acid Content and Descendents; U.S. Pat. No. 5,534,425 Soybeans Having Low Linolenic Acid Content and Method of Production; U.S. Pat. No. 5,750,844 Soybeans capable of forming a vegetable oil having specified concentrations of palmitic and stearic acids; U.S. Pat. No. 5,750,845 Soybeans capable of forming a vegetable oil having a low saturated fatty acid content; U.S. Pat. No. 5,585,535 Soybeans and Soybean Products Having Low Palmitic Acid Content; U.S. Pat. No. 5,850,029 Soybean Designated AX7017-1-3; U.S. Pat. No. 5,663,485 Soybean Designated A89-259098; U.S. Pat. No. 5,684,230 Soybean designated AX 4663-5-4-5; U.S. Pat. No. 5,684,231 Soybean designated A1937 NMU-85; U.S. Pat. No. 5,714,672 Soybean Designated ElginEMS-421; U.S. Pat. No. 5,602,311 Soybeans and Soybean Products Having High Palmitic Acid Content; U.S. Pat. No. 5,795,969 Soybean Vegetable Oil Having Elevated Concentrations of Both Palmitic and Stearic Acid; U.S. Pat. No. 5,557,037 Soybeans Having Elevated Contents of Saturated Fatty Acids; U.S. Pat. No. 5,516,980 Soybean Variety XB37ZA; U.S. Pat. No. 5,530,183 Soybean Variety 9253; U.S. Pat. No. 5,750,846 Elevated Palmitic Acid Production in Soybeans; U.S. Pat. No. 6,060,647 Elevated Palmitic Acid Production in Soybeans; U.S. Pat. No. 6,025,509 Elevated Palmitic Acid Production in Soybeans; U.S. Pat. No. 6,133,509 Reduced Linolenic Acid Production in Soybeans; U.S. Pat. No. 5,986,118 Soybean Vegetable Oil Possessing a Reduced Linolenic Acid Content; U.S. Pat. No. 5,850,030 Reduced Linolenic Acid Production in Soybeans). Industrial uses of soybean oil that is subjected to further processing include ingredients for paints, plastics, fibers, detergents, cosmetics, and lubricants. Soybean oil may be split, inter-esterified, sulfurized, epoxidized, polymerized, ethoxylated, or cleaved. Designing and producing soybean oil derivatives with improved functionality, oliochemistry is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein. For human consumption soybean meal is made into soybean flour that is processed to protein concentrates used for meat extenders or specialty pet foods. Production of edible protein ingredients from soybean offers a healthy, less expensive replacement for animal protein in meats as well as dairy-type products.

DEPOSIT INFORMATION

Applicants have made a deposit of at least 2500 seeds of soybean cultivar S06-02JR409114 with the American Type Culture Collection (ATCC), Manassas, Va. 20110 on Nov. 3, 2008 and designated PTA-9571. The seeds were tested on Nov. 17, 2008 and found viable. Access to this deposit will be available during the pendency of the application to the Commissioner for Patents and persons determined by the Commissioner to be entitled thereto upon request. Upon granting of a patent on any claims in the application, the Applicants will make the deposit available to the public pursuant to 37 CFR §1.808. Additionally, Applicants will meet the requirements of 37 CFR §1.801-1.809, including providing an indication of the viability of the sample when the deposit is made. The ATCC deposit will be maintained in that depository, which is a public depository, for a period of 30 years, or 5 years after the last request, or for the enforceable life of the patent, whichever is longer, and will be replaced if it becomes nonviable during that period.

Accordingly, the present invention has been described with some degree of particularity directed to the preferred embodiment of the present invention. It should be appreciated, though that the present invention is defined by the following claims construed in light of the prior art so that modifications or changes may be made to the preferred embodiment of the present invention without departing from the inventive concepts contained herein.

What is claimed is:

1. A soybean seed designated S06-02JR409114, a sample of said seed deposited under ATCC Accession No. PTA-9571.

2. A plant, or parts thereof, produced by growing the seed of claim 1.

3. Pollen of the plant of claim 2.

4. A soybean plant, or parts thereof, having all of the physiological and morphological characteristics of the soybean plant of claim 2.

5. A tissue culture of regenerable cells of the soybean plant of claim 2.

6. The tissue culture according to claim 5, wherein the cells are obtained from the group consisting of leaf, pollen, embryo, meristematic cell, root, root tip, anther, stomatal cell, flower, seed, stem and pod.

7. A soybean plant regenerated from the tissue culture of claim 6, having all of the morphological and physiological characteristics of soybean cultivar S06-02JR409114.

8. A method for producing a soybean seed comprising crossing two soybean plants and harvesting the resultant soybean seed, wherein at least one soybean plant is the soybean plant of claim 2.

9. A method for producing a hybrid soybean seed comprising crossing the soybean plant according to claim 2 with a second soybean plant and harvesting the resultant hybrid soybean seed.

10. A method for producing a S06-02JR409114-derived soybean plant, comprising:
   a) crossing soybean line S06-02JR409114, a sample of said line deposited under ATCC Accession No. PTA-9571, with a second soybean plant to yield progeny soybean seed; and
   b) growing said progeny soybean seed to yield said S06-02JR409114-derived soybean plant.

11. The method of claim 8, wherein the second soybean plant is transgenic.

12. The method of claim 11 wherein the transgenic soybean plant contains transgenetic material conferring a trait selected from the group consisting of herbicide resistance, nematode resistance, insect resistance, resistance to disease, and male sterility.

13. The method of claim 12 wherein the resistance to disease is through an oxalate oxidase encoding polynucleotide sequence or an oxalate decarboxylase encoding polynucleotide sequence.

14. A S06-02JR409114-derived soybean plant produced by the method of claim 10.

15. A transgenic soybean plant produced by the method of claim 12, wherein said transgenic soybean plant comprises the trait selected from the group consisting of herbicide resistance, insect resistance, resistance to disease and male sterility.

* * * * *